(12) United States Patent
Broom

(10) Patent No.: US 9,011,488 B2
(45) Date of Patent: Apr. 21, 2015

(54) METHOD OF CLOSURE FOR THORACOTOMY AND THORASCOPY INCISIONS

(71) Applicant: Covidien LP, Mansfield, MA (US)

(72) Inventor: Daniel Broom, Branford, CT (US)

(73) Assignee: Covidien LP, Mansfield, MA (US)

( * ) Notice: Subject to any disclaimer, the term of this patent is extended or adjusted under 35 U.S.C. 154(b) by 199 days.

(21) Appl. No.: 13/647,733

(22) Filed: Oct. 9, 2012

(65) Prior Publication Data

US 2014/0100607 A1 Apr. 10, 2014

(51) Int. Cl.
*A61L 17/00* (2006.01)
*A61B 17/06* (2006.01)
*A61B 17/70* (2006.01)
*A61B 17/00* (2006.01)

(52) U.S. Cl.
CPC ..... *A61B 17/06166* (2013.01); *A61B 17/06066* (2013.01); *A61B 2017/00889* (2013.01); *A61B 2017/06057* (2013.01); *A61B 2017/06176* (2013.01); *A61B 17/707* (2013.01)

(58) Field of Classification Search
CPC ............ A61B 17/06; A61B 17/06166; A61B 2017/06171
USPC ......................................... 606/222, 228, 148
See application file for complete search history.

(56) References Cited

U.S. PATENT DOCUMENTS

2003/0029462 A1* 2/2003 Cox et al. ...................... 128/898
2010/0160725 A1* 6/2010 Kiser et al. .................... 600/104

\* cited by examiner

*Primary Examiner* — Victor Nguyen

(57) ABSTRACT

A method of closing a thoracic incision includes providing a barbed suture and threading the suture around first and second ribs of a chest wall in a generally S-shaped configuration to close an incision positioned therebetween. The barbed suture is threaded through the chest wall by introducing the barbed suture through a first terminal tissue layer and around a surface of the first rib that is facing a second terminal tissue layer, passing the barbed suture across the incision and around a surface of the second rib that is facing the first terminal tissue layer, and withdrawing the barbed suture through the second terminal tissue layer. A second barbed suture may be threaded through the chest wall in a complementary S-shaped configuration in which the second barbed suture enters and exits the chest wall through the opposing terminal tissue layer from that of the first barbed suture.

10 Claims, 3 Drawing Sheets

METHOD OF CLOSURE FOR THORACOTOMY AND THORASCOPY INCISIONS

BACKGROUND

1. Technical Field

The present disclosure relates to surgical methods, and more particularly, to a surgical method for wound closure.

2. Background of Related Art

Both open and minimally invasive surgical techniques are utilized to investigate and treat the organs and tissues in the chest cavity. Traditionally, with open surgery, a large incision (thoracotomy) is required to open the chest. The incision may extend between the ribs, and the ribs are spread apart to access the thoracic space. While smaller incisions are utilized with less invasive surgical options, in some procedures, such as thorascopy, the incisions may still be made between adjacent ribs to access the chest cavity.

Incisions are typically closed with wound closure devices, such as sutures and/or staples. One common closure technique involves looping suture material around the ribs adjacent to the incision. This closure type may give rise to pressure and pinching on the intercostal nerves which lie near the ribs and cause acute and/or chronic pain. Other known methods of closure may be considered nerve sparing, and involve drilling holes into one or more ribs and passing sutures therethrough to limit intercostal nerve compression.

It would be advantageous to provide a surgical wound closure method that preserves the intercostal nerves, and eliminates the need for knot tying of sutures loops, as well as additional tissue manipulation, such as drilling, to simplify and shorten the time to close an opening, thereby limiting and/or preventing post-operative pain.

SUMMARY

A method of closing a thoracic incision includes providing a unidirectional barbed suture and threading the barbed suture around a first rib and a second rib of a chest wall in a generally S-shaped configuration to close an incision positioned therebetween. The barbed suture is threaded through the chest wall by introducing the barbed suture through a first terminal tissue layer and around a surface of the first rib that is facing a second terminal tissue layer, passing the barbed suture across the incision and around a surface of the second rib that is facing the first terminal tissue layer and withdrawing the barbed suture through the second terminal tissue layer. A needle may be secured to the barbed suture to penetrate and guide the passage of the barbed suture through the chest wall.

A plurality of barbed sutures may be provided and threaded around the first and second ribs in a generally S-shaped configuration in spaced relation to each other along the length of the incision. In embodiments, the plurality of sutures may be aligned in substantially parallel relation to each other. In other embodiments, adjacent sutures may be crossed with each through the incision in a generally X-shaped configuration.

A second barbed suture may be paired with the first barbed suture and threaded through the chest wall in a complementary S-shaped configuration in which the second barbed suture enters and exits the chest wall through the opposing terminal tissue layer from that of the first barbed suture.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1:
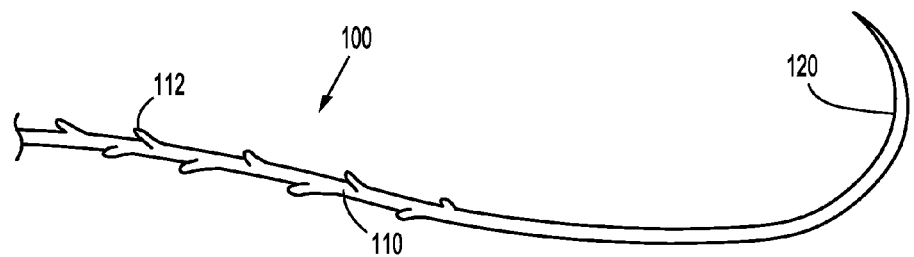
FIG. 1 is a perspective view of a barbed suture for use in an embodiment of the surgical method of the present disclosure.

A method of closing a thoracic incision is described herein. While the present discussion and figures below depict exemplary embodiments of the present disclosure in terms of wound closure techniques for use in thoracic surgery, the presently disclosed surgical method may be utilized in any surgical or medical procedure requiring closure of wounds in the body. Additionally, the disclosed method may be utilized to fix tissue and/or materials within the chest wall, the thoracic or other body cavity. The use of the term "tissue" hereinbelow should be understood to encompass the tissue surrounding a patient's ribs, such as muscle, fat, fascia, and/or skin.

Initially, the surgical method includes providing a barbed suture. The barbed suture described herein may be formed from any sterilizable biocompatible material that has suitable physical properties for the intended use of the device. The suture may be fabricated from any biodegradable and/or non-biodegradable polymeric and/or metallic material that can be used in surgical procedures.

The term "biodegradable" as used herein is defined to include both bioabsorbable and bioresorbable materials. By biodegradable, it is meant that the material decomposes, or loses structural integrity under body conditions (e.g., enzymatic degradation or hydrolysis) or is broken down (physically or chemically) under physiologic conditions in the body such that the degradation products are excretable or absorbable by the body. Absorbable materials are absorbed by biological tissues and disappear in vivo at the end of a given period, which can vary, for example, from hours to several months, depending on the chemical nature of the material. It should be understood that such materials include natural, synthetic, bioabsorbable, and/or certain non-absorbable materials, as well as combinations thereof.

Representative natural biodegradable polymers include: polysaccharides such as alginate, dextran, chitin, chitosan, hyaluronic acid, cellulose, collagen, gelatin, fucans, glycosaminoglycans, and chemical derivatives thereof (substitutions and/or additions of chemical groups include, for example, alkyl, alkylene, amine, sulfate, hydroxylations, carboxylations, oxidations, and other modifications routinely made by those skilled in the art); catgut; silk; linen; cotton; and proteins such as albumin, casein, zein, silk, soybean protein, and copolymers and blends thereof; alone or in combination with synthetic polymers.

Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, and cellulose sulfate sodium salt.

Representative synthetic biodegradable polymers include: polyhydroxy acids prepared from lactone monomers such as glycolide, lactide, caprolactone, ϵ-caprolactone, valerolactone, and δ-valerolactone, carbonates (e.g., trimethylene carbonate, tetramethylene carbonate, and the like), dioxanones (e.g., 1,4-dioxanone and p-dioxanone), 1,dioxepanones (e.g., 1,4-dioxepan-2-one and 1,5-dioxepan-2-one), and combinations thereof. Polymers formed therefrom include: polylactides; poly(lactic acid); polyglycolides; poly(glycolic acid); poly(trimethylene carbonate); poly(dioxanone); poly(hydroxybutyric acid); poly(hydroxyvaleric acid); poly(lactide-co-(ϵ-caprolactone-)); poly(glycolide-co-(ϵ-caprolactone)); polycarbonates; poly(pseudo amino acids); poly(amino acids); poly(hydroxyalkanoate)s such as polyhydroxybutyrate, polyhydroxyvalerate, poly(3-hydroxybutyrate-co-3-hydroxyvalerate), polyhydroxyoctanoate, and polyhydroxyhexanoate; polyalkylene oxalates; polyoxaesters; polyanhydrides; polyester anyhydrides; polyortho esters; and copolymers, block copolymers, homopolymers, blends, and combinations thereof.

Some non-limiting examples of suitable non-degradable materials include: polyolefins such as polyethylene (including ultra high molecular weight polyethylene) and polypropylene including atactic, isotactic, syndiotactic, and blends thereof; polyethylene glycols; polyethylene oxides; polyisobutylene and ethylene-alpha olefin copolymers; fluorinated polyolefins such as fluoroethylenes, fluoropropylenes, fluoroPEGSs, and polytetrafluoroethylene; polyamides such as nylon, Nylon 6, Nylon 6,6, Nylon 6,10, Nylon 11, Nylon 12, and polycaprolactam; polyamines; polyimines; polyesters such as polyethylene terephthalate, polyethylene naphthalate, polytrimethylene terephthalate, and polybutylene terephthalate; polyethers; polybutester; polytetramethylene ether glycol; 1,4-butanediol; polyurethanes; acrylic polymers; methacrylics; vinyl halide polymers such as polyvinyl chloride; polyvinyl alcohols; polyvinyl ethers such as polyvinyl methyl ether; polyvinylidene halides such as polyvinylidene fluoride and polyvinylidene chloride; polychlorofluoroethylene; polyacrylonitrile; polyaryletherketones; polyvinyl ketones; polyvinyl aromatics such as polystyrene; polyvinyl esters such as polyvinyl acetate; etheylene-methyl methacrylate copolymers; acrylonitrile-styrene copolymers; ABS resins; ethylene-vinyl acetate copolymers; alkyd resins; polycarbonates; polyoxymethylenes; polyphosphazine; polyimides; epoxy resins; aramids; rayon; rayon-triacetate; spandex; silicones; and copolymers and combinations thereof.

In embodiments, the suture may include: metals such as steel or titanium; metal alloys including degradable alloys such as iron-based or magnesium-based degradable alloys; and the like.

The suture includes a suture body formed from at least one filament that is fabricated from natural, synthetic, degradable, and/or non-degradable materials, as well as combinations thereof, as described above. The filament(s) may be formed using any technique within the purview of those skilled in the art such as, for example, extrusion, molding, casting, and/or spinning. The filament(s) may also be drawn, oriented, annealed, calendared, crinkled, twisted, commingled, crimped, or air entangled to form the suture body.

The suture may include single and/or compound barbs formed along a portion or the entire length of the filament(s) in specified or random patterns. Barbs may be formed from angled cuts in an outer surface of a filament, or barbs may be molded on the outer surface of a filament, such that an inner surface of the barb is positioned opposite to an outer surface of a filament. The barbs may all be oriented in the same or different directions, and may be cut at the same or different barb angles. Compound barbs include an inner surface including at least two angled cuts disposed at first and second orientations, respectively, relative to a longitudinal axis of the suture body. Examples of compound barbs which may be utilized include those disclosed in U.S. Patent Application Publication No. 2009/0210006, entitled "Compound Barb Medical Device and Method", the entire disclosure of which is incorporated by reference herein.

The barbs can be arranged in any suitable pattern, for example, in a helical pattern. The number, configuration, and spacing of the barbs can vary depending upon the tissue in which the suture is used, as well as the composition and geometry of the material utilized to form the suture. Additionally, the proportions of the barbs may remain relatively constant while the overall length of the barbs, number, and spacing of the barbs may be determined by the tissue being connected.

The surface area of the barbs may also vary. For example, fuller-tipped barbs can be made of varying sizes designed for specific surgical applications. When joining fat and relatively soft tissues, large barbs may be desired, whereas smaller barbs may be more suitable for collagen-dense tissues. In some embodiments, a combination of large and small barbs on the same structure may be beneficial, for example, when used in a tissue repair with differing tissue layer structures. A combination of large and small barbs may be used within the same suture such that the barb sizes are customized for each tissue layer to ensure maximum holding properties.

The suture may be coated. The coating may be utilized to alter the physical properties on the surface of the suture (e.g., enhance lubricity), or may provide a therapeutic benefit to tissue. In general, a coating may be applied to a surface of the suture, or selective regions thereof, by, for example, spraying, dipping, brushing, vapor deposition, co-extrusion, capillary wicking, film casting, molding, etc.

A variety of therapeutic agents may be coated on the suture, or incorporated into the suture. Therapeutic agents include any substance or mixture of substances that have clinical use. Alternatively, a therapeutic agent could be any agent which provides a therapeutic or prophylactic effect; a compound that affects or participates in tissue growth, cell growth and/or cell differentiation; a compound that may be able to invoke or prevent a biological action such as an immune response; or a compound that could play any other role in one or more biological processes. Moreover, any agent which may enhance tissue repair, limit the risk of sepsis, and modulate the mechanical properties of the tissue fixation device (e.g., the swelling rate in water, tensile strength, etc.) may be added to the material forming the suture or may be coated thereon.

Examples of classes of therapeutic agents which may be utilized in accordance with the present disclosure include antimicrobials, analgesics, antipyretics, anesthetics, antiepileptics, antihistamines, anti-inflammatories, cardiovascular drugs, diagnostic agents, sympathomimetics, cholinomimetics, antimuscarinics, antispasmodics, hormones, growth factors, muscle relaxants, adrenergic neuron blockers, antineoplastics, immunogenic agents, immunosuppressants, gastrointestinal drugs, diuretics, steroids, lipids, lipopolysaccharides, polysaccharides, and enzymes. It is also intended that combinations of therapeutic agents may be used.

Other therapeutic agents which may be in the present disclosure include: local anesthetics; non-steroidal antifertility agents; parasympathomimetic agents; psychotherapeutic agents; tranquilizers; decongestants; sedative hypnotics; steroids; sulfonamides; sympathomimetic agents; vaccines; vitamins; antimalarials; anti-migraine agents; anti-parkinson agents such as L-dopa; anti-spasmodics; anticholinergic agents (e.g., oxybutynin); antitussives; bronchodilators; cardiovascular agents such as coronary vasodilators and nitroglycerin; alkaloids; analgesics; narcotics such as codeine, dihydrocodeinone, meperidine, morphine and the like; non-narcotics such as salicylates, aspirin, acetaminophen, d-propoxyphene and the like; opioid receptor antagonists such as naltrexone and naloxone; anti-cancer agents; anti-convulsants; anti-emetics; antihistamines; anti-inflammatory agents such as hormonal agents, hydrocortisone, prednisolone, prednisone, non-hormonal agents, allopurinol, indomethacin, phenylbutazone and the like; prostaglandins and cytotoxic drugs; estrogens; antibacterials; antibiotics; anti-fungals; anti-virals; anticoagulants; anticonvulsants; antidepressants; antihistamines; and immunological agents.

Other examples of suitable therapeutic agents which may be included in the suture include: viruses and cells; peptides, polypeptides and proteins, as well as analogs, muteins, and active fragments thereof; immunoglobulins; antibodies; cytokines (e.g., lymphokines, monokines, chemokines); blood clotting factors; hemopoietic factors; interleukins (IL-2, IL-3, IL-4, IL-6); interferons (β-IFN, (α-IFN and γ-IFN)); erythropoietin; nucleases; tumor necrosis factor; colony stimulating factors (e.g., GCSF, GM-CSF, MCSF); insulin; anti-tumor agents and tumor suppressors; blood proteins; gonadotropins (e.g., FSH, LH, CG, etc.); hormones and hormone analogs (e.g., growth hormone); vaccines (e.g., tumoral, bacterial and viral antigens); somatostatin; antigens; blood coagulation factors; growth factors (e.g., nerve growth factor, insulin-like growth factor); protein inhibitors; protein antagonists; protein agonists; nucleic acids such as antisense molecules, DNA, and RNA; oligonucleotides; and ribozymes.

In embodiments, a suture may be attached to a needle. The needle may be curved or straight, and fabricated from an absorbable or non-absorbable material, such as those described above with respect to the suture, having suitable strength characteristics to introduce and pass the suture through tissue. The needle may be releasable secured to the suture, and may have an eyelet, slot, barb, crimp, or other retention means for securing the suture thereto. It should be understood, however, that any device capable of passing a suture through tissue may be utilized in the wound closure method of the present disclosure.

As illustrated in FIG. 1, suture 100 includes an elongated suture body 110 including a plurality of barbs 112 aligned in a single direction to form a unidirectional barbed suture. The alignment of the barbs 112 allows the suture 100 to move through tissue in one direction and prevents movement of the suture 100 relative to tissue in a direction opposite to the direction of movement of the suture 100. A needle 120 may be attached to the suture 100 for penetrating and guiding the passage of the suture 100 through tissue.

Figure 2:
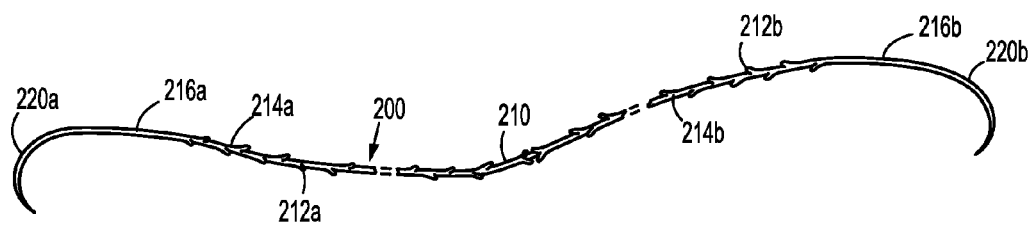
FIG. 2 is a perspective view of a barbed suture for use in another embodiment of the surgical method of the present disclosure.

FIG. 2 illustrates suture 200 including an elongated body 210 having a first body portion 214a including a first distal end 216a and a second body portion 214b including a second distal end 216b. A plurality of barbs 212a extend from the first body portion 214a to permit movement of the first body portion 214a of the suture 200 through tissue in one direction and prevent movement of the suture 200 relative to the tissue in a direction opposite to the direction of movement of the first body portion 214a. A plurality of barbs 212b extend from the second body portion 214b to permit movement of the second body portion 214b of the suture 200 through tissue in a single direction of movement and prevent movement of the suture 200 relative to the tissue in a direction opposite to the direction of movement of the second body portion 214b. First and second needles 220a and 220b may be attached to first and second distal ends 216a and 216b of the suture 200, respectively, for penetrating tissue and guiding the passage of the first and second body portions 214a and 214b of the suture 200 through tissue.

Figure 3:
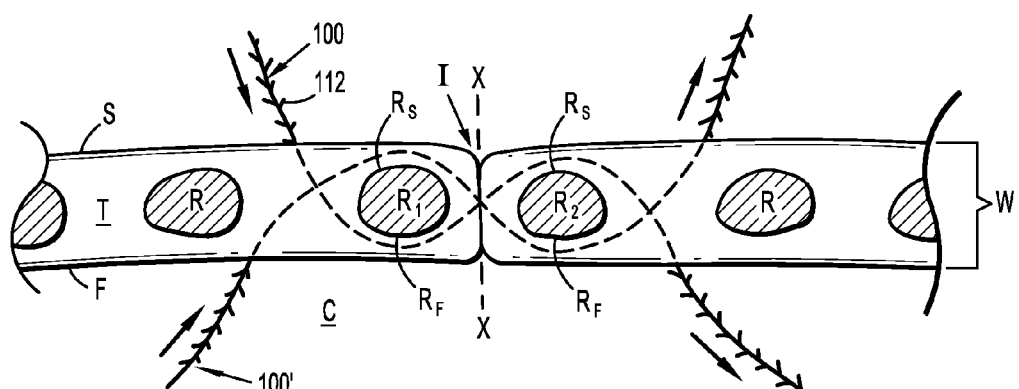
FIG. 3 is a cross-sectional view of a chest wall including an incision that has been closed in accordance with an embodiment of the surgical method of the present disclosure.

After a suture is selected, the suture is then threaded through a chest wall to close an incision. FIG. 3 illustrates a side view of a chest wall including an incision closed via a wound closure method of the present disclosure. Chest wall "W" covers thoracic cavity "C", and includes two terminal tissue layers, skin "S" and endothoracic fascia "F" facing thoracic cavity "C". Ribs "R" are positioned within internal tissue "T" within the chest wall "W". Each rib "R" includes a skin facing surface "$R_S$" and a fascia facing surface "$R_F$". An incision "I" extends along a longitudinal axis "X" between ribs "$R_1$" and "$R_2$" that are adjacent the incision "I".

A first suture, such as the unidirectional barbed suture 100 of FIG. 1, is passed through the chest wall "W" in a sinusoidal or S-shaped configuration. First suture 100 is introduced into the chest wall "W" through skin "S" into internal tissue "T" towards the thoracic cavity "C". The first suture 100 is then passed around the fascia facing surface "$R_F$" of rib "$R_1$", through incision "I", and around skin facing surface "$R_S$" of rib "$R_2$" before exiting fascia "F". The end(s) of the first suture 100 extending through skin "S" and fascia "F" may then be cut. The self-fixating nature of the barbs 112 of the first suture 100 removes the need for surgical knots, enhances healing by apposing the edges of the incision "I" without placing the tissue "T" under tension, and minimizes strangulation of the intercostal nerves and vessels.

First suture 100 may be paired with second suture 100' which may be threaded in a complementary sinusoidal or s-shaped configuration. By "complementary" it is meant that the first and second sutures 100 and 100' enter and exit on opposite sides of the chest wall "W" and cross through incision "I". As illustrated, second suture 100' is passed through fascia "F" into internal tissue "T" towards skin "S". The second suture 100' is then passed around the skin facing surface "$R_S$" of rib "$R_1$", through incision "I", and around fascia facing surface "$R_F$" of rib "$R_2$" before exiting skin "S". The end(s) of the second suture 100' extending through skin "S" and fascia "F" may then be cut.

Figure 4:
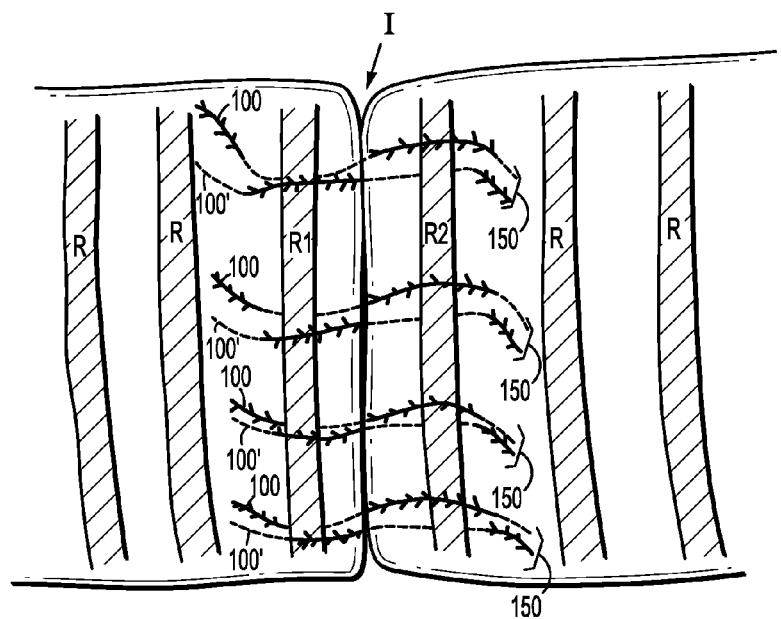
FIG. 4 is a top view of a chest wall including an incision that has been closed in accordance with an embodiment of the surgical method of the present disclosure.
Figure 5:
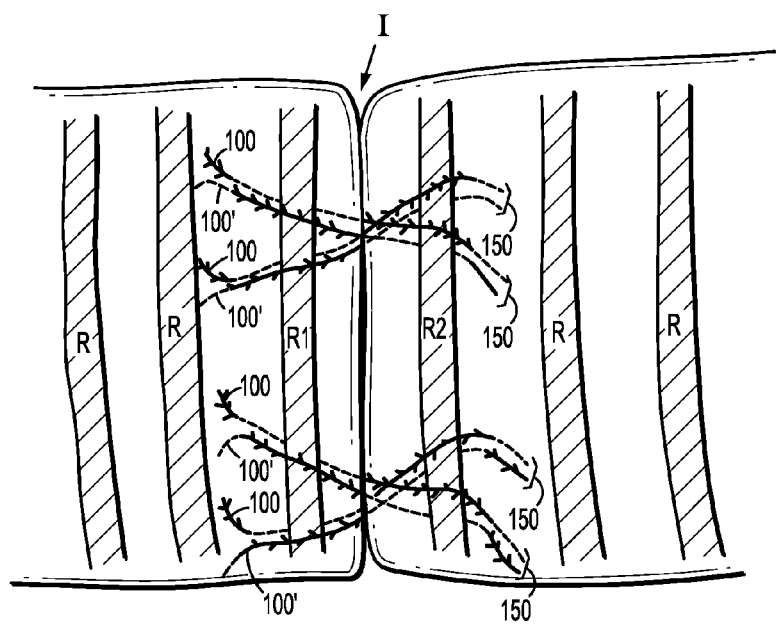
FIG. 5 is a top view of a chest wall including an incision that has been closed in accordance with another embodiment of the surgical method of the present disclosure.

A plurality of paired sutures 100 and 100' may be placed along the length of the incision "I" as illustrated in FIG. 4. FIG. 4 illustrates a plurality of sets 150 of paired sutures 100 and 100' extending in substantially parallel relation to each other along the length of the incision "I". Alternatively, as illustrated in FIG. 5, a set 150 of paired sutures 100 and 100' may be paired with an adjacent set 150 of paired sutures 100 and 100' so that they cross each other in an X-shaped configuration across incision "I". It should be understood that sutures 100 and/or 100' may be passed around additional ribs depending upon the strength of closure required.

Figure 6:
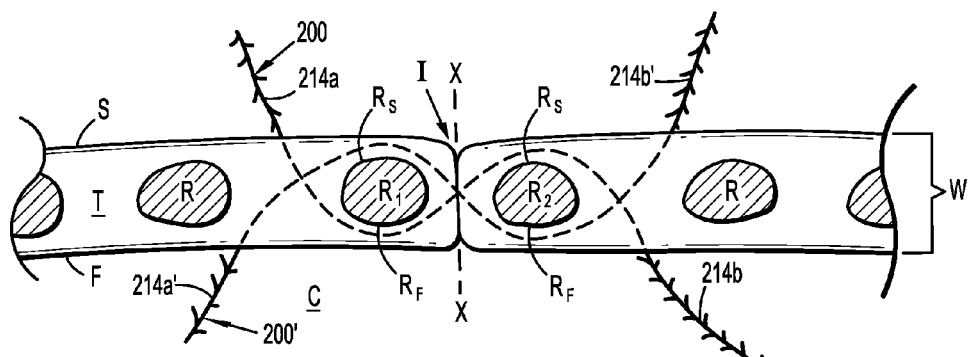
FIG. 6 is a cross-sectional view of a chest wall including an incision that has been closed in accordance with yet another embodiment of the surgical method of the present disclosure.

In an alternative embodiment, illustrated in FIG. 6, a first bi-directional suture 200 may be utilized to close incision "I". Similar to the wound closure method discussed above with respect to unidirectional barbed suture 100, bi-directional barbed suture 200 is threaded through the chest wall "W" in a sinusoidal or S-shaped configuration. Suture 200 is initially positioned within incision "I". First body portion 214a is passed from the incision "I", into tissue "T", around the fascia facing surface "$R_F$" of rib "$R_1$", and out through skin "S". Second body portion 214b is passed from the incision "I", through tissue "T", around the skin facing surface "$R_S$" of rib "$R_2$", and out through endothoracic fascia "F". Thereafter, the ends of the first and second body portions 214a and 214b may be cut to the surface of the skin "S" and endothoracic fascia "F", respectively.

Figure 7:
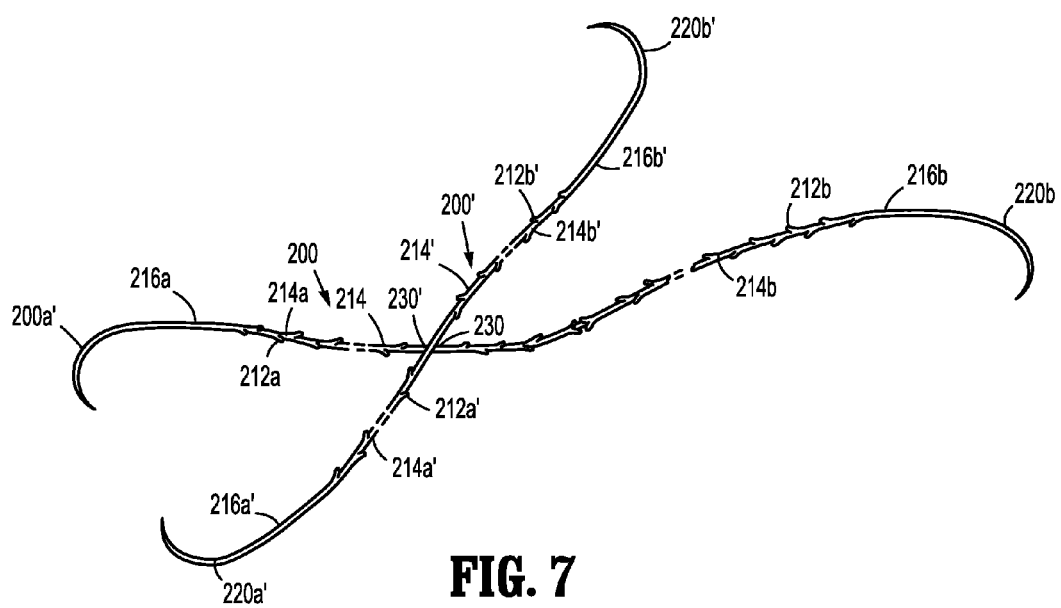
FIG. 7 is a perspective view of a barbed suture for use in an embodiment of the surgical method of the present disclosure.

First bi-directional suture 200 may be paired with a second bi-directional suture 200' which is threaded in a complementary sinusoidal or s-shaped configuration. Second suture 200' is similarly positioned within incision "I", with first body portion 214a' passed through tissue "T" around the skin facing surface "$R_s$" of rib "$R_1$" and out through endothoracic fascia "F" and second body portion 214b' passed through tissue "T" around the fascia facing surface "$R_F$" of rib "$R_2$" and out through skin "S". In embodiments, the first and second bi-directional sutures 200 and 200' may be joined at barb transition point 230 and 230', respectively, as illustrated in FIG. 7, prior to placement within incision "I". Sets of bi-directional sutures 200 and 200' may be positioned along the length of incision "I" in a parallel or crossed configuration similar to those of FIGS. 4 and 5.

Persons skilled in the art will understand that the devices and methods specifically described herein, and illustrated in the accompanying drawings, are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosed devices and methods based on the above-described embodiments. As such, further modifications and equivalents of the invention herein disclosed can occur to persons skilled in the art using no more than routine experimentation, and all such modifications and equivalents are believed to be within the spirit and scope of the disclosure as defined by the following claims.

What is claimed is:

1. A method of closing a thoracic incision, the method comprising:
   threading a first barbed suture of a set of barbed sutures around a first rib and a second rib of a chest wall in a generally S-shaped configuration to close an incision positioned therebetween by:
   introducing a leading end of the first barbed suture into the chest wall through a first terminal tissue layer and around a surface of the first rib that is facing a second terminal tissue layer;
   passing the leading end of the first barbed suture across the incision and around a surface of the second rib that is facing the first terminal tissue layer; and
   withdrawing the leading end of the first barbed suture from the chest wall through the second terminal tissue layer; and
   threading a second barbed suture of the set of barbed sutures around the first rib and the second rib in a generally S-shaped configuration that is complementary to the first barbed suture by:
   introducing a leading end of the second barbed suture into the chest wall through the second terminal tissue layer and around a surface of the first rib that is facing the first terminal tissue layer;
   passing the leading end of the second barbed suture across the incision and around a surface of the second rib that is facing the second terminal tissue layer; and
   withdrawing the leading end of the second barbed suture from the chest wall through the first terminal tissue layer.

2. The method of claim 1, further comprising:
   penetrating and guiding the passage of the first and second barbed sutures through the chest wall using needles attached to the leading ends of the first and second barbed sutures.

3. The method of claim 1, further comprising:
   threading a plurality of sets of barbed sutures through the chest wall and across the incision.

4. The method of claim 3, wherein threading the plurality of sets of barbed sutures further comprises:
   aligning the plurality of sets of barbed sutures in substantially parallel relation to each other.

5. The method of claim 3, further comprising:
   crossing adjacent sets of barbed sutures of the plurality of sets of barbed sutures through the incision in a generally X-shaped configuration.

6. A method of closing a thoracic incision, the method comprising:
   threading first and second barbed sutures of a first set of sutures around a first rib, across an incision positioned in a chest wall between the first rib and a second rib, and around the second rib in complementary S-shaped configurations; wherein threading the first and second barbed sutures of the first set of sutures includes: introducing leading ends of the first and second barbed sutures through opposed tissue layers of the chest wall and through tissue disposed around opposed surfaces of the first rib; passing the leading ends of the first and second barbed sutures across the incision and through tissue disposed around opposed surfaces of the second rib; and withdrawing the leading ends of the first and second barbed sutures though the other of the opposed tissue layers of the chest wall through which the first and second barbed sutures were introduced.

7. The method of claim 6, wherein threading the first and second barbed sutures of the first set of sutures further includes:
   guiding the first and second barbed sutures through the chest wall with needles attached to the leading ends of the first and second barbed sutures.

8. The method of claim 6, further comprising:
   threading first and second barbed sutures of a second set of sutures around the first rib, across the incision, and around the second rib in complementary S-shaped configurations.

9. The method of claim 8, wherein threading the first and second barbed sutures of the second set of sutures further includes:
   aligning the second set of sutures in substantially parallel relation to the first set of sutures.

10. The method of claim 8, wherein threading the first and second barbed sutures of the second set of sutures further includes:
    crossing the second set of sutures over the first set of sutures in a generally X-shaped configuration across the incision.

* * * * *